(12) United States Patent
Abe et al.

(10) Patent No.: US 8,143,033 B2
(45) Date of Patent: Mar. 27, 2012

(54) PROCESS FOR PRODUCING (METH)ACRYLAMIDE

(75) Inventors: Takeya Abe, Takaishi (JP); Takeshi Fukuda, Takaishi (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 478 days.

(21) Appl. No.: 12/301,138

(22) PCT Filed: Apr. 3, 2007

(86) PCT No.: PCT/JP2007/057436
§ 371 (c)(1),
(2), (4) Date: Nov. 17, 2008

(87) PCT Pub. No.: WO2007/132601
PCT Pub. Date: Nov. 22, 2007

(65) Prior Publication Data
US 2009/0311759 A1    Dec. 17, 2009

(30) Foreign Application Priority Data

May 15, 2006 (JP) ................................. 2006-135813

(51) Int. Cl.
*C12P 13/02* (2006.01)
(52) U.S. Cl. ....................................................... 435/129
(58) Field of Classification Search .................... 435/129
See application file for complete search history.

(56) References Cited

U.S. PATENT DOCUMENTS

| 4,001,081 A | 1/1977 | Commeyras et al. |
| 4,313,001 A | 1/1982 | Itoh et al. |
| 4,637,982 A * | 1/1987 | Yamada et al. ............... 435/129 |
| 4,701,558 A | 10/1987 | Yamaguchi et al. |
| 7,592,165 B2 | 9/2009 | Osswald et al. |
| 2002/0160466 A1 | 10/2002 | Abe et al. |
| 2007/0077634 A1 * | 4/2007 | Hughes et al. ................ 435/129 |
| 2009/0269822 A1 * | 10/2009 | Hughes et al. ................ 435/129 |

FOREIGN PATENT DOCUMENTS

| GB | 2 018 240 A | 10/1979 |
| JP | 56-92254 A | 7/1981 |
| JP | 56-104852 A | 8/1981 |
| JP | 61-115495 A | 6/1986 |
| JP | 61-122253 A | 6/1986 |
| JP | 5-15384 A | 1/1993 |
| JP | 9-227478 A | 9/1997 |
| JP | 2001-340091 A | 12/2001 |
| JP | 2005-289840 A | 10/2005 |
| WO | WO 03/033716 A1 | 4/2003 |
| WO | WO 2005/090394 | 9/2005 |

OTHER PUBLICATIONS

Office Action issued in corresponding Australian Patent Application No. 2007/7251017 dated Feb. 10, 2010.
International Search Report (PCT/ISA/210).

* cited by examiner

*Primary Examiner* — Herbert J Lilling
(74) *Attorney, Agent, or Firm* — Buchanan Ingersoll & Rooney PC

(57) ABSTRACT

A process for producing (meth)acrylamide using a microbial catalyst, wherein production steps can be simplified and production cost can be reduced. The process for producing (meth)acrylamide of the present involves (a) a step of allowing (meth)acrylonitrile to undergo hydration reaction by the use of a microbial catalyst containing nitrile hydratase in an aqueous medium to obtain a (meth)acrylamide reaction solution (I) and (b) a step of removing impurities from the reaction solution (I) to obtain a (meth)acrylamide aqueous solution (II), wherein the concentration of (meth)acrylamide in the reaction solution (I) obtained in the step (a) is higher than the concentration of (meth)acrylamide in the aqueous solution (II) obtained in the step (b) by 2 to 20% by weight.

1 Claim, No Drawings

US 8,143,033 B2

PROCESS FOR PRODUCING (METH)ACRYLAMIDE

TECHNICAL FIELD

The present invention relates to a process for producing (meth)acrylamide. More particularly, the invention relates to a process for producing (meth)acrylamide comprising allowing (meth)acrylonitrile to undergo hydration reaction by the use of a microbial catalyst containing nitrile hydratase in an aqueous medium.

BACKGROUND ART (Meth)acrylamide is a compound useful as a raw material of a (meth)acrylamide-based polymer, and particularly, an acrylamide-based polymer is widely used as a paper strength increasing agent, a coagulant or the like.

In recent years, as a process for producing (meth)acrylamide, a process using a microbial catalyst instead of a copper catalyst has been paid attention because it has advantages such that the reaction conditions are mild and the amounts of by-products are extremely small (see patent document 1). In this process, (meth)acrylonitrile is hydrated by an enzyme contained in the microorganism, i.e., nitrile hydratase, and thereby converted into (meth)acrylamide. Through this process, acrylamide is obtained as an aqueous solution of 40 to 80% by weight, and methacrylamide is obtained as an aqueous solution of 10 to 40% by weight. When the resulting (meth)acrylamide is used as a raw material of a (meth)acrylamide-based polymer, acrylamide is preferably supplied as an aqueous solution of 40 to 60% by weight or a crystalline product, and methacrylamide is preferably supplied as an aqueous solution of 10 to 20% by weight or a crystalline product.

In the case where such a (meth)acrylamide aqueous solution as above is produced using a biocatalyst, and if (meth)acrylamide is introduced in a concentration lower than the concentration in the end product to the subsequent step of performing separation of impurities such as a microbial catalyst, there occurs a problem that the concentration of (meth)acrylamide is further lowered in the subsequent step. Therefore, it becomes necessary to perform a step of adjusting the concentration of (meth)acrylamide to that in the end product, such as a water removal step by distillation or the like, after the above-mentioned subsequent step of performing separation of impurities. Further, there is another problem that such a removal step leads to an increase in production cost.

Also in the case where such a crystalline product of (meth)acrylamide as above is produced, it is necessary to increase a concentration ratio or to decrease a crystallization temperature in order to obtain a difference in concentration required for crystallization, so that there is a problem of an increase in cost.

Patent document 1: Pamphlet of International Publication No. 2003/033716

DISCLOSURE OF THE INVENTION

Problem to be Solved by the Invention

It is an object of the present invention to provide a process for producing (meth)acrylamide wherein production steps can be simplified and production cost can be reduced by the use of a microbial catalyst containing nitrile hydratase.

Means to Solve the Problem

As a result of earnest studies, the present inventors have found that the aforesaid problems can be solved by obtaining a reaction solution containing (meth)acrylamide in a specific concentration by the use of a microbial catalyst, and they have achieved the present invention.

That is to say, the process for producing (meth)acrylamide according to the present invention is a process for producing (meth)acrylamide comprising:

(a) a step of allowing (meth)acrylonitrile to undergo hydration reaction by the use of a microbial catalyst containing nitrile hydratase in an aqueous medium to obtain a (meth)acrylamide reaction solution (I), and (b) a step of removing impurities from the reaction solution (I) to obtain a (meth)acrylamide aqueous solution (II), wherein the concentration of (meth)acrylamide in the reaction solution (I) obtained in the step (a) is higher than the concentration of (meth)acrylamide in the aqueous solution (II) obtained in the step (b) by 2 to 20% by weight.

Effect of the Invention

According to the present invention, a process for producing (meth)acrylamide wherein production steps can be simplified and production cost can be reduced by the use of a microbial catalyst containing nitrile hydratase is provided.

BEST MODE FOR CARRYING OUT THE INVENTION

The present invention is described in detail hereinafter.
Production of (Meth)Acrylamide In the step (a), (meth)acrylonitrile is allowed to undergo hydration reaction by the use of a microbial catalyst containing nitrile hydratase in an aqueous medium, whereby a (meth)acrylamide reaction solution (I) is obtained.

The aqueous medium for use in the invention means water or an aqueous solution in which a buffering agent such as phosphate, an inorganic salt such as sulfate or carbonate, a hydroxide of an alkali metal, an amide compound or the like is dissolved in an appropriate concentration. When acrylonitrile and the microbial catalyst are added in the form of aqueous solutions as described later, aqueous media in these aqueous solutions are also included in the above aqueous media.

In the present invention, commercially available (meth)acrylonitrile is properly used, but it is preferable to use (meth)acrylonitrile from which impurities have been removed.

Examples of methods to remove impurities from (meth)acrylonitrile include distillation purification, washing with an alkali aqueous solution, removal of impurities by the use of an ion-exchange resin such as a cation-exchange resin or an anion-exchange resin, and removal of impurities by the use of activated carbon. By the use of such (meth)acrylonitrile, (meth)acrylamide can be obtained more efficiently.

In the hydration reaction, (meth)acrylonitrile may be used as it is, or may be used after it is dissolved in water or mixed with water.

The microorganism containing nitrile hydratase for use in the invention is not specifically restricted provided that the microorganism produces nitrile hydratase. The nitrile hydratase referred to herein is an enzyme having an ability to hydrate a nitrile compound such as acrylonitrile to form the corresponding amide compound such as acrylamide.

Examples of the microorganisms include microorganisms belonging to genus *Nocardia*, genus *Corynebacterium*, genus *Bacillus*, thermophilic genus *Bacillus*, genus *Pseudomonas*, genus *Micrococcus*, genus *Rhodococcus* represented by *rhodochrous* species, genus *Acinetobacter*, genus *Xanthobacter*, genus *Streptomyces*, genus *Rhizobium*, genus *Kleb-*

*siella*, genus *Enterobacter*, genus *Erwinia*, genus *Aeromonas*, genus *Citrobacter*, genus *Achromobacter*, genus *Agrobacterium*, and genus *Pseudonocardia* represented by *thermophila* species. These microorganisms may be used singly or in combination of two or more kinds.

In the microorganisms, transformation products obtained by developing nitrile hydratase genes having been cloned from the above microorganisms in arbitrary hosts are also included. Examples of the arbitrary hosts referred to herein include *Escherichia coli*; bacteria of genus *Bacillus* such as *Bacillus subtilis*; and strains of other microorganisms such as yeast and actinomycetes. An example of such a strain is MT-10822, and this strain has been deposited with an accession number of FERM BP-5785 to National Institute of Bioscience and Human-Technology, Agency of Industrial Science and Technology, the Ministry of International Trade and Industry, 1-3, Higashi 1-chome, Tsukuba-shi, Ibaraki-ken (present: International Patent Organism Depositary, National Institute of Advanced Industrial Science and Technology, Independent Administrative Institution) on Feb. 7, 1996, under the Budapest treaty on the International Recognition of the Deposit of Microorganisms for the Purpose of Patent Procedure.

Further, transformation products wherein variant type nitrile hydratase improved in acrylamide resistance, acrylonitrile resistance and temperature resistance is developed by means of replacement of one or more constituent amino acids of the enzyme with other amino acids, deficiency thereof, deletion thereof or insertion thereof utilizing recombinant DNA technology are also included in the microorganisms referred to in the invention.

The microbial catalysts containing nitrile hydratase for use in the invention include not only microorganism bacterial cells obtained by culturing such microorganisms as above but also substances obtained by treating bacterial cells, such as an extract of the microorganism bacterial cell, a ground substance of the microorganism bacterial cell, an after-separated substance obtained by separating and purifying a nitrile hydratase active fraction of the extract or the ground substance, and a fixed substance obtained by fixing the microorganism bacterial cell, the extract of the bacterial cell, the ground substance of the bacterial cell, the after-separated substance or the like onto an appropriate carrier. As described above, the microbial catalyst may be a microbial catalyst that is soluble in an aqueous solution or may be a solid matter fixed onto a carrier. The above microbial catalysts may be used singly, or two or more kinds of them may be used simultaneously or alternately. In the microbial catalysts containing nitrile hydratase, moreover, a solution containing at least one of the above microbial catalysts, such as a mixed solution or a buffer solution, a suspension containing at least one of the above microbial catalysts, etc. are also included. The form of the microbial catalyst used is properly selected according to stability of nitrile hydratase, production scale, etc.

Such a microorganism as mentioned above is prepared by a publicly known method. For example, such a microorganism is obtained by planting the microorganism in a liquid culture medium such as LB culture medium or M9 culture medium, then growing it at an appropriate culture temperature (it is generally 20° C. to 50° C., but it may be not lower than 50° C. in the case of thermophilic bacteria), subsequently separating the microorganism from the culture solution by centrifugation and recovering the microorganism.

In the step (a), the (meth)acrylonitrile is allowed to undergo hydration reaction by the use of the microbial catalyst in the aqueous medium to obtain a (meth)acrylamide reaction solution (I) having a desired concentration. This hydration reaction is carried out in a conventional manner, and for example, the reaction can be carried out in the following manner.

In the present invention, the concentration of the (meth) acrylonitrile is not specifically restricted provided that the (meth)acrylamide reaction solution (I) of a desired concentration is obtained. Although the upper limit of the concentration of the (meth)acrylonitrile is not specifically restricted, feed of excess (meth)acrylonitrile needs a large catalytic amount for completion of the reaction, a reactor having an excess volume and an excess heat exchanger for removal of heat, so that the economical burden in the equipment aspect becomes heavy.

On this account, the amount of the (meth)acrylonitrile fed is as follows. In the case of acrylonitrile, it is preferable to feed acrylonitrile in such an amount that the theoretical produced solution concentration of acrylamide in the reaction solution (I) in the reactor becomes 42 to 80% by weight when all the acrylonitile becomes the corresponding acrylamide. More specifically, it is preferable to feed acrylonitrile in an amount of 0.4 to 1.5 parts by weight based on 1 part by weight of the aqueous medium.

In the case of methacrylonitrile, it is preferable to feed methacrylonitrile in such an amount that the theoretical produced solution concentration of methacrylamide in the reaction solution (I) in the reactor becomes 12 to 40% by weight when all the methacrylonitile becomes the corresponding methacrylamide. More specifically, it is preferable to feed methacrylonitrile in an amount of 0.09 to 0.5 part by weight based on 1 part by weight of the aqueous medium.

The microbial catalyst may be used in any amount provided that the (meth)acrylamide reaction solution (I) of a desired concentration is obtained, and the amount thereof is properly determined according to the reaction conditions, the type of the catalyst and the form thereof. However, the amount of the microbial catalyst is in the range of usually 10 to 50000 ppm by weight, preferably 50 to 30000 ppm by weight, in terms of weight of dry bacterial cell, based on the aqueous medium.

The reaction time of the hydration reaction is not specifically restricted either provided that the (meth)acrylamide reaction solution (I) of a desired concentration is obtained. Although the reaction time depends upon the amount of the catalyst used and the conditions such as temperature, it is specifically in the range of usually 1 to 80 hours, preferably 2 to 40 hours, based on one reactor.

Although the hydration reaction is usually carried out at atmospheric pressure, it may be carried out under pressure in order to increase solubility of the (meth)acrylonitrile in the aqueous medium. The reaction temperature is not specifically restricted provided that it is not lower than the ice point of the aqueous medium. However, it is desirable to carry out the reaction at a temperature of usually 0 to 50° C., preferably 10 to 40° C. The pH value of the aqueous medium in the hydration reaction is not specifically restricted and may be any value provided that the activity of nitrile hydratase is maintained. However, the pH value of the aqueous medium is desired to be in the range of preferably 6 to 10, more preferably 7 to 9. The hydration reaction may be carried out by any of a batch process and a continuous process, and the reaction may be carried out by selecting its reaction system from reaction systems of a suspended bed, a fixed bed, a fluidized bed and the like or by combining different reaction systems according to the form of the catalyst.

Through such hydration reaction, the (meth)acrylamide reaction solution (I) is obtained. In this reaction solution (I), (meth)acrylamide, the aqueous medium, the microbial catalyst dissolved are contained, and in addition, solid matters such as the microbial catalyst fixed onto a carrier and dead bacterial cells are sometimes contained.

The concentration of (meth)acrylamide in the reaction solution (I) obtained in the step (a) is as follows. In the case of acrylamide, the concentration is in the range of usually 42 to 80% by weight, and in the case of methacrylamide, the concentration is in the range of usually 12 to 40% by weight.

In the step (b), impurities are removed from the mixture obtained in the step (a), whereby a (meth)acrylamide aqueous solution (II) is obtained.

Examples of the impurities include the dissolved microbial catalyst, and solid matters, such as the microbial catalyst fixed onto a carrier and dead bacterial cells.

As a method to remove the dissolved microbial catalyst, a method comprising bringing the reaction solution (I) into contact with activated carbon in an acidic atmosphere and removing the activated carbon is preferably used, as described in Japanese Patent Laid-Open Publication No. 270857/2001. In the above contact, an aqueous solution for adjusting pH may be added to the (meth)acrylamide reaction solution, and when the activated carbon is removed by filtration, wash water may be added to the (meth)acrylamide reaction solution. Consequently, the concentration of (meth)acrylamide is lowered in the step (b).

For removing the solid matters, filtration, centrifugation, film separation, ion-exchange resin, etc. may be used. In the case of, for example, filtration, wash water is added to the (meth)acrylamide reaction solution, and consequently, the concentration of (meth)acrylamide is lowered in the step (b).

Through the above step, the (meth)acrylamide aqueous solution (II) wherein impurities have been removed from the reaction solution (I) obtained in the step (a) is obtained. In order to use the aqueous solution (II) obtained in this step (b) as a raw material of a (meth)acrylamide-based polymer, the concentration of (meth)acrylamide in the aqueous solution (II) obtained in the step (b) is as follows. In the case of acrylamide, the concentration is in the range of usually 40 to 60% by weight, and in the case of methacrylamide, the concentration is in the range of usually 10 to 20% by weight.

The concentration of (meth)acrylamide in the reaction solution or the aqueous solution can be measured by a conventional method, such as high performance liquid chromatography, gas chromatography or a method of using a refractometer, and in the present specification, the concentration is measured by high performance liquid chromatography as in the working example.

As described above, the present invention is characterized in that the concentration of (meth)acrylamide in the reaction solution (I) obtained in the step (a) is higher than the concentration of (meth)acrylamide in the aqueous solution (II) obtained in the step (b) by 2 to 20% by weight. That is to say, in the step (a), a reaction solution (I) containing (meth)acrylamide in an amount larger by the above value is prepared. On this account, the concentration of (meth)acrylamide in the reaction solution is lowered by filtration or the like in the step (b). Therefore, even if the aqueous solution (II) obtained in the step (b) is not subjected to a step of removing water by distillation of water or the like, the aqueous solution can be favorably used as an end product of an aqueous solution, or in the case of a crystalline product, the aqueous solution can be favorably used as a stock solution for crystallization.

Accordingly, in the process for producing (meth)acrylamide of the invention, not only simplification of production steps can be promoted but also production cost can be reduced.

The (meth)acrylamide aqueous solution (II) produced may be purified by further subjecting it to a step of, for example, concentration, ion exchange, crystallization or treatment with activated carbon.

Production of (Meth)Acrylamide-Based Polymer

The (meth)acrylamide obtained in the invention can be subjected to homopolymerization or copolymerization, or it can be copolymerized with other monomers.

Examples of the other monomers copolymerizable with the (meth)acrylamide include:

unsaturated carboxylic acids, such as acrylic acid, methacrylic acid, itaconic acid, maleic acid and fumaric acid, and salts thereof;

vinylsulfonic acid, styrenesulfonic acid, acrylamidomethylpropanesulfonic acid, and salts thereof;

alkylaminoalkyl esters of (meth)acrylic acid, such as N,N-dimethylaminoethyl methacrylate, N,N-diethylaminoethyl methacrylate and N,N-dimethylaminoethyl acrylate, and quaternary ammonium derivatives thereof;

N,N-dialkylaminoalkyl (meth)acrylamides, such as N,N-dimethylaminopropyl methacrylamide and N,N-dimethylaminopropyl acrylamide, and quaternary ammonium derivatives thereof;

hydrophilic acrylamides, such as acetone acrylamide, N,N-dimethyl acrylamide, N,N-dimethyl methacrylamide, N-ethyl methacrylamide, N-ethyl acrylamide, N,N-diethyl acrylamide and N-propyl acrylamide;

N-acryloylpyrrolidine, N-acryloylpiperidine and N-acryloylmorpholine;

hydroxyethyl methacrylate, hydroxyethyl acrylate, hydroxypropyl methacrylate and hydroxypropyl acrylate;

methoxypolyethylene glycol (meth)acrylate and N-vinyl-2-pyrrolidone;

N-alkyl (meth)acrylamide derivatives, such as N,N-di-n-propyl acrylamide, N-n-butyl acrylamide, N-n-hexyl acrylamide, N-n-hexyl methacrylamide, N-n-octyl acrylamide, N-n-octyl methacrylamide, N-tert-octyl acrylamide, N-dodecyl acrylamide and N-n-dodecyl methacrylamide;

N-(ω-glycidoxyalkyl)(meth)acrylamide derivatives, such as N,N-diglycidyl acrylamide, N,N-diglycidyl methacrylamide, N-(4-glycidoxybutyl)acrylamide, N-(4-glycidoxybutyl)methacrylamide, N-(5-glycidoxypentyl)acrylamide and N-(6-glycidoxyhexyl)acrylamide;

(meth)acrylate derivatives, such as methyl (meth)acrylate, ethyl (meth)acrylate, butyl (meth)acrylate, lauryl (meth)acrylate, 2-ethylhexyl (meth)acrylate and glycidyl (meth)acrylate; and acrylonitrile, methacrylonitrile, vinyl acetate, vinyl chloride, vinylidene chloride, olefins, such as ethylene, propylene and butene, styrene, α-methylstyrene, butadiene and isoprene.

These monomers may be used singly or as a mixture of two or more kinds. Further, the acrylamide, the methacrylamide and the above-mentioned other monomers may be copolymerized.

In the case where the (meth)acrylamide and the above monomers are copolymerized, their mixing ratio is not specifically restricted, but in usual, the monomers are used in amounts of not more than 100 mol, preferably not more than 50 mol, based on 100 mol of the (meth)acrylamide.

The process for producing the acrylamide-based polymer is not specifically restricted and can be carried out by a known method such as aqueous solution polymerization or emulsion polymerization. However, the aqueous solution polymerization using a radical polymerization initiator is preferably employed. In the case of the aqueous solution polymerization, the total concentration of the acrylamide and a monomer that is added when necessary is desired to be in the range of usually 5 to 90% by weight.

The polymerization initiator used is, for example, a radical polymerization initiator, and examples thereof include peroxides, such as potassium persulfate, ammonium persulfate, hydrogen peroxide and benzoyl peroxide; azo type free radical initiators, such as azobisisobutyronitrile, 2,2'-azobis(4-amidinopropane)dihydrochloride and 4,4'-azobis(sodium 4-cyanovalerianate); and redox type catalysts using the above peroxides in combination with reducing agents such as sodium bisulfite, triethanolamine and ammonium ferrous sulfate.

The above polymerization initiators may be used singly or may be used in combination of two or more kinds. The amount of the polymerization initiator is in the range of usually 0.001 to 5% by weight based on the total weight of the monomers.

The polymerization temperature is in the range of usually −10 to 120° C., more preferably 0 to 90° C. The polymerization temperature does not need to be always maintained at a constant temperature, and it may be properly changed with the progress of polymerization. In usual, with the progress of polymerization, heat of polymerization is generated, and the polymerization temperature tends to rise, so that the polymerization system is sometimes cooled when necessary.

The atmosphere in the polymerization is not specifically restricted, but from the viewpoint that the polymerization is allowed to proceed rapidly, the polymerization is preferably carried out in an atmosphere of an inert gas such as a nitrogen gas.

Although the polymerization time is not specifically restricted, it is in the range of usually 1 to 20 hours.

Although pH of the aqueous solution in the polymerization is not specifically restricted either, the pH may be adjusted to carry out polymerization, when necessary. Examples of pH adjustors employable in this case include alkalis, such as sodium hydroxide, potassium hydroxide and ammonia; mineral acids, such as phosphoric acid, sulfuric acid and hydrochloric acid; and organic acids, such as formic acid and acetic acid.

Although the molecular weight of the polymer obtained as above is not specifically restricted, it is in the range of usually 100,000 to 50,000,000, preferably 500,000 to 30,000,000.

Since the (meth)acrylamide obtained by the invention has excellent quality, the (meth)acrylamide-based polymer obtained by the above process is markedly improved in water solubility and has a sufficiently high molecular weight. Moreover, the resulting polymer is excellent also in color tone. Accordingly, this (meth)acrylaimde-based polymer can be favorably used as a coagulant, an additive for paper manufacturing, a petroleum recovering agent or the like.

The present invention is further described with reference to the following examples, but it should be construed that the invention is in no way limited to those examples.

EXAMPLE 1

Culture of Bacterial Cell Containing Nitrile Hydratase

A No. 3 clone bacterial cell was obtained in accordance with a method described in Example 1 of Japanese Patent Laid-Open Publication No. 340091/2001, and the bacterial cell was cultured by the method of the same Example 1 to obtain a wet bacterial cell containing nitrile hydratase.

Preparation of Acrylamide

In order to obtain an aqueous solution product having an acrylamide concentration of 50% by weight as an end product, reaction was carried out under the following conditions.

A 1-liter glass flask equipped with a stirrer was prepared as a first reactor, and a Teflon (registered trademark) tube having an inner diameter of 5 mm and a length of 20 m was prepared as a second reactor. In the first reactor, 400 g of water was placed in advance.

The wet bacterial cell obtained by the above culture method was suspended in pure water. This suspension was continuously fed to the first reactor at a rate of 11 g/hr with stirring the contents of the reactor. Acrylonitrile was continuously fed at a rate of 32 g/hr, and pure water was continuously fed at a rate of 37 g/hr. Further, a 0.1M NaOH aqueous solution was fed so that the reaction pH would become 7.5 to 8.5. These raw materials were fed through independent lines from their respective reservoirs, and they did not contact with one another until they were fed into the reactor. In order to keep the liquid level in the first reactor constant, the reaction solution was continuously drawn out of the first reactor at a rate of 80 g/hr and continuously fed to the second reactor, and in the second reactor, the reaction was further promoted.

The first reactor and the second reactor were both immersed in a water bath at a temperature of 10 to 20° C., and temperature control was carried out so that the solution temperature in each of the reactors would become 15° C.

On the second day from the beginning of operation, the reaction solution (reaction solution (I)) in each reactor was sampled, and the sample was analyzed under the following HPLC conditions. As a result, the conversion to acrylamide at the outlet of the first reactor was 87%, the acrylonitrile concentration at the outlet of the second reactor was not more than the detection limit (not more than 100 ppm by weight), and the acrylamide concentration at the outlet of the second reactor was 53.5% by weight.

The analysis conditions are as follows.

Acrylamide Analysis Conditions

High performance liquid chromatograph: LC-10A system (manufactured by Shimadzu Corporation, UV detector wavelength: 250 nm, column temperature: 40° C.)

Separation column: SCR-101H (manufactured by Shimadzu Corporation)

Eluting solution: 0.05% (volume basis) phosphoric acid aqueous solution

Acrylonitrile Analysis Conditions

High performance liquid chromatograph: LC-10A system (manufactured by Shimadzu Corporation, UV detector wavelength: 200 nm, column temperature: 40° C.)

Separation column: Wakosil-II 5C18HG (manufactured by Wako Pure Chemical industries, Ltd.)

Eluting solution: aqueous solution containing 7% (volume basis) acetonitrile, 0.1 mM acetic acid and 0.2 mM sodium acetate in each concentration The acrylamide concentration was determined in the following manner. Commercially available acrylamide was dissolved in pure water to prepare an acrylamide aqueous solution having a known concentration, and a calibration curve for the acrylamide concentration analysis in HPLC was prepared. Using the calibration curve, the area value of the test liquid in the HPLC analysis was converted into an acrylamide concentration (absolute calibration curve method). The amount of the reaction solution used in the HPLC measurement was 5 μL. Since the density of each reaction solution hardly had influence, the acrylamide concentration (% by weight) was obtained in this manner.

On the second day from the beginning of the reaction, the analysis was carried out, and thereafter the reaction was further continued for about 4 days. In these about 4 days, about 7500 g of a reaction solution (reaction solution (I)) was obtained. To the solution, 30 g of activated carbon (powdery activated carbon PM-SX available from Mitsukura Chemical Co., Ltd.) was added, and then 160 g of a 0.5 wt % acrylic acid aqueous solution was added. Thereafter, using a 1M NaOH aqueous solution, pH of the resulting solution was adjusted to 5. After the solution was stirred for 5 hours at 25° C., it was filtered through a filter paper to remove activated carbon. Thereafter, in order to recover acrylamide having adhered to the activated carbon, the activated carbon was washed with 300 g of pure water, and the wash water was mixed with the aforesaid solution having been treated with activated carbon. The mixed solution was neutralized with a 1M NaOH aqueous solution to adjust pH to 7. Thus, about 7900 g of a product (aqueous solution (II)) was obtained. The final acrylamide concentration in the product (aqueous solution (II)) obtained after the activated carbon treatment was 50.6% by weight, and this value was more than 50.0% by weight that was an aimed concentration.

COMPARATIVE EXAMPLE 1

Quite the same procedure as in Example 1 was carried out, except that the feed rate of the acrylonitrile was changed to 30 g/hr and the feed rate of pure water was changed to 39 g/hr. As a result, the acrylamide concentration in the resulting reaction solution was 50.2% by weight. The final acrylamide concentration in the product (aqueous solution) obtained after the activated carbon treatment was 47.1% by weight, and this value was less than 50.0% by weight that was an aimed concentration. On this account, it became necessary to perform treatment for obtaining a concentration for the end product, e.g., water removal treatment by distillation or the like.

The invention claimed is:

1. A process for producing (meth)acrylamide, comprising:
    (a) a step of allowing (meth)acrylonitrile to undergo hydration reaction by the use of a microbial catalyst containing nitrile hydratase in an aqueous medium to obtain a (meth)acrylamide reaction solution (I), and
    (b) a step of removing impurities from the reaction solution (I) to obtain a (meth)acrylamide aqueous solution (II),
    wherein the concentration of (meth)acrylamide in the reaction solution (I) obtained in the step (a) is higher than the concentration of (meth)acrylamide in the aqueous solution (II) obtained in the step (b) by 2 to 20% by weight; wherein the (meth)acrylonitrile is acrylonitrile and the (meth)acrylamide is acrylamide; and the concentration of the acrylamide in the aqueous solution (II) is 40 to 60% by weight.

* * * * *